United States Patent
Suzuki et al.

(10) Patent No.: US 9,427,213 B2
(45) Date of Patent: Aug. 30, 2016

(54) BREAST MEASUREMENT APPARATUS

(75) Inventors: Toshihiko Suzuki, Hamamatsu (JP); Yutaka Yamashita, Hamamatsu (JP); Yukio Ueda, Hamamatsu (JP); Etsuko Yamaki, Hamamatsu (JP); Daisuke Yamashita, Hamamatsu (JP); Kenji Yoshimoto, Hamamatsu (JP); Harumi Sakahara, Hamamatsu (JP); Hiroyuki Ogura, Hamamatsu (JP); Hatsuko Nasu, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 660 days.

(21) Appl. No.: 13/880,569

(22) PCT Filed: Oct. 18, 2011

(86) PCT No.: PCT/JP2011/073950
§ 371 (c)(1),
(2), (4) Date: Jun. 12, 2013

(87) PCT Pub. No.: WO2012/053518
PCT Pub. Date: Apr. 26, 2012

(65) Prior Publication Data
US 2013/0253322 A1    Sep. 26, 2013

(30) Foreign Application Priority Data
Oct. 22, 2010  (JP) ................................ 2010-237726

(51) Int. Cl.
*A61B 5/00* (2006.01)
*A61B 8/08* (2006.01)
(Continued)

(52) U.S. Cl.
CPC .......... *A61B 8/5261* (2013.01); *A61B 5/0035* (2013.01); *A61B 5/0073* (2013.01);
(Continued)

(58) Field of Classification Search
None
See application file for complete search history.

(56) References Cited

U.S. PATENT DOCUMENTS 4,282,880 A * 8/1981 Gardineer .............. A61B 8/406
128/915
4,681,120 A * 7/1987 Kunii ................... A61B 8/0825
128/915
(Continued)

FOREIGN PATENT DOCUMENTS

CN       1575770       2/2005
CN     101427940       5/2009
(Continued)

OTHER PUBLICATIONS

Aloka, Ltd., "Ultrasonic diagnosis apparatus image gallery, product information", http://www.hitachi-aloka.co.jp/english/products/show_gallery.html [Formerly http://www.aloka.co.jp/products/show_gallery.html], retrieved on Sep. 8, 2010.

*Primary Examiner* — Long V Le
*Assistant Examiner* — Bradley Impink
(74) *Attorney, Agent, or Firm* — Drinker Biddle & Reath LLP (57) ABSTRACT

A breast measurement apparatus comprises a receptacle for surrounding a breast; a plurality of optical fibers for irradiating the breast with examination light and detecting transmitted scattered light from the breast; an inner image generation unit for generating an optical CT image concerning the breast according to a detection signal of the transmitted scattered light; an ultrasonic probe, arranged so as to face the inside of the receptacle, for scanning the breast with an ultrasonic wave and receiving a reflected wave from the breast; an image generation unit for generating an ultrasonic image concerning the breast according to the reflected wave; and a mechanism for injecting and discharging a liquid interface agent into and from the inside of the receptacle.

8 Claims, 7 Drawing Sheets

(51) Int. Cl.
*A61B 8/00* (2006.01)
*A61B 8/14* (2006.01)
*A61B 10/00* (2006.01)

(52) U.S. Cl.
CPC ............ *A61B5/0091* (2013.01); *A61B 5/4312* (2013.01); *A61B 5/6835* (2013.01); *A61B 5/708* (2013.01); *A61B 5/72* (2013.01); *A61B 8/0825* (2013.01); *A61B 8/14* (2013.01); *A61B 8/406* (2013.01); *A61B 8/4227* (2013.01); *A61B 8/4281* (2013.01); *A61B 8/4416* (2013.01); *A61B 8/4444* (2013.01); *A61B 8/4455* (2013.01); *A61B 8/4477* (2013.01); *A61B 8/5207* (2013.01); *A61B 10/0041* (2013.01); *A61B 5/7425* (2013.01); *A61B 2562/146* (2013.01)

(56) References Cited

U.S. PATENT DOCUMENTS

| | | | | |
|---|---|---|---|---|
| 5,293,873 A | * | 3/1994 | Fang | A61B 5/0091 600/437 |
| 6,146,377 A | * | 11/2000 | Lee | A61B 8/0825 600/414 |
| 6,409,668 B1 | * | 6/2002 | Wollschlaeger | A61B 8/406 600/443 |
| 2002/0099287 A1 | * | 7/2002 | Ohmae | A61B 5/0091 600/425 |
| 2002/0188198 A1 | * | 12/2002 | Hong | A61B 8/0825 600/437 |
| 2004/0215072 A1 | * | 10/2004 | Zhu | A61B 5/0091 600/407 |
| 2009/0262365 A1 | | 10/2009 | Da Silva et al. | |
| 2010/0073674 A1 | * | 3/2010 | Yoshida | A61B 5/0073 356/300 |
| 2010/0094134 A1 | * | 4/2010 | Zhu | A61B 5/0073 600/473 |

FOREIGN PATENT DOCUMENTS

| | | |
|---|---|---|
| CN | 101523203 | 9/2009 |
| EP | 2036487 | 3/2009 |
| JP | 2-239849 A | 9/1990 |
| JP | 11-173976 A | 7/1999 |
| JP | 2009068962 A | 4/2009 |
| JP | 2009090074 A | 4/2009 |
| JP | 2009225904 A | 10/2009 |
| JP | 2010094500 A | 4/2010 |

* cited by examiner

BREAST MEASUREMENT APPARATUS

TECHNICAL FIELD

The present invention relates to a breast measurement apparatus.

BACKGROUND ART

Typical X-ray mammography apparatus widely in use for breast cancer examinations irradiate parts to be examined of subjects with X-rays, capture images of transmitted X-rays, so as to acquire internal information of the parts, which is used as diagnostic information for breast cancer. However, in fear of the X-ray radiation affecting living bodies, systems which irradiate parts to be examined with light, ultrasonic waves, and the like and detect intensities of transmitted scattered light (diffused reflected light) and reflected ultrasonic waves, so as to acquire internal information of the parts have recently been introduced into clinical use or under study (see, for example, Non Patent Literature 1).

CITATION LIST

Non Patent Literature

Non Patent Literature 1: Ultrasonic diagnosis apparatus image gallery, product information, Aloka Ltd. [online] [retrieved on 2010-09-08]. Retrieved from the Internet: <URL: http://www.aloka.co.jp/products/show_gallery.html>.

SUMMARY OF INVENTION

Technical Problem

The inventors have developed a breast measurement apparatus based on diffused light tomography (optical CT: Computed Tomography) using near-infrared rays and faced the following problem. Recent studies have resulted in the optical CT yielding high-resolution images, which, as a consequence, have also been found to generate deviations in positions of tumors and the like between an image obtained by other image diagnosis apparatus (such as MRI and ultrasonic diagnosis apparatus) and an optical CT image. This seems to be because of the fact that, while the optical CT apparatus arranges a liquid interface agent having an optical coefficient such as light-scattering coefficient substantially on a par with that of breasts around the breasts, the other image diagnosis apparatus perform measurement in the atmosphere, so that measurement conditions vary between the optical CT and the other image diagnosis apparatus. It is therefore difficult to compare the optical CT images with images of other image diagnosis apparatus, thereby making it hard to evaluate the optical CT images.

It is an object of the present invention to provide a breast measurement apparatus which can simultaneously acquire an ultrasonic image of another image diagnosis apparatus and an optical CT image under the same measurement condition.

Solution to Problem

The breast measurement apparatus in accordance with one aspect of the present invention is a breast measurement apparatus for acquiring an inner image of a breast of a subject, the apparatus comprising a receptacle for surrounding the breast; a plurality of optical fibers, arranged so as to face the inside of the receptacle, for irradiating the breast with examination light and detecting transmitted scattered light (diffused reflected light) from the breast; a first inner image generation unit for generating a first inner image concerning the breast according to a detection signal of the transmitted scattered light; a probe, arranged so as to face the inside of the receptacle, for scanning the breast with an ultrasonic wave and receiving a reflected wave from the breast; a second inner image generation unit for generating a second inner image concerning the breast according to the reflected wave; and a mechanism for injecting and discharging a liquid interface agent into and from the inside of the receptacle.

In this breast measurement apparatus, a probe for scanning a breast with an ultrasonic wave is arranged in addition to a plurality of optical fibers for optical CT in the receptacle surrounding the breast. This makes it possible to acquire an optical CT image and an ultrasonic image simultaneously under the same measurement condition.

The receptacle in the breast measurement apparatus may include a material transmitting the ultrasonic wave therethrough and satisfying a boundary condition of a light propagation model for the examination light. This makes it possible to achieve both of optical CT measurement and ultrasonic measurement favorably within a single receptacle. In this case, the receptacle (an inner wall part thereof in particular) may include a material such as a resin which transmits the ultrasonic wave therethrough.

A contour of the breast may be extracted as three-dimensional coordinates, for example, from the acquired second inner image (ultrasonic image) and used as forecast information for reconstructing an optical CT image. Since the gap between the receptacle and the breast is filled with the interface agent having a known optical characteristic (e.g., absorption coefficient, equivalent scattering coefficient, or refractive index), a minimum unit (voxel) of imaging can be provided beforehand with the optical characteristic as forecast information when reconstructing the optical CT image. This can further limit the imaging range, whereby the accuracy in image reconstruction within the breast can be expected to improve.

The breast measurement apparatus may further comprise an image combination unit for combining (e.g., superimposing) the acquired ultrasonic image (second inner image) and optical CT image (first inner image) together, which allows a doctor to observe size-matched anatomical and functional images at the same time, whereby the accuracy in diagnosing breast cancer can be expected to improve.

The breast measurement apparatus may further comprise a mechanism for making a distance variable between the probe and the breast. The breast measurement apparatus may further comprise a mechanism for rotating the probe about an axis passing through the breast. These can reduce an area deviating from a measurement region of an ultrasonic diagnosis apparatus within the receptacle.

The breast measurement apparatus may further comprise a deaerator for deaerating the interface agent. This can inhibit ultrasonic noises from occurring in the interface agent and enhance the accuracy in ultrasonic measurement. On the other hand, it is optically important to eliminate bubbles, since they optically distort the measurement light propagating through the interface agent in optical measurement and impart errors to the measurement light having measured the breast. Thus, the deaerator performs important actions for both ultrasonic measurement and optical measurement.

Advantageous Effects of Invention

The breast measurement apparatus in accordance with the present invention can acquire an optical CT image and an ultrasonic image under the same measurement condition.

DESCRIPTION OF EMBODIMENTS

In the following, embodiments of the breast measurement apparatus will be explained in detail with reference to the accompanying drawings. In the explanation of the drawings, the same or equivalent parts will be referred to with the same signs while omitting their overlapping descriptions.

Figure 1:
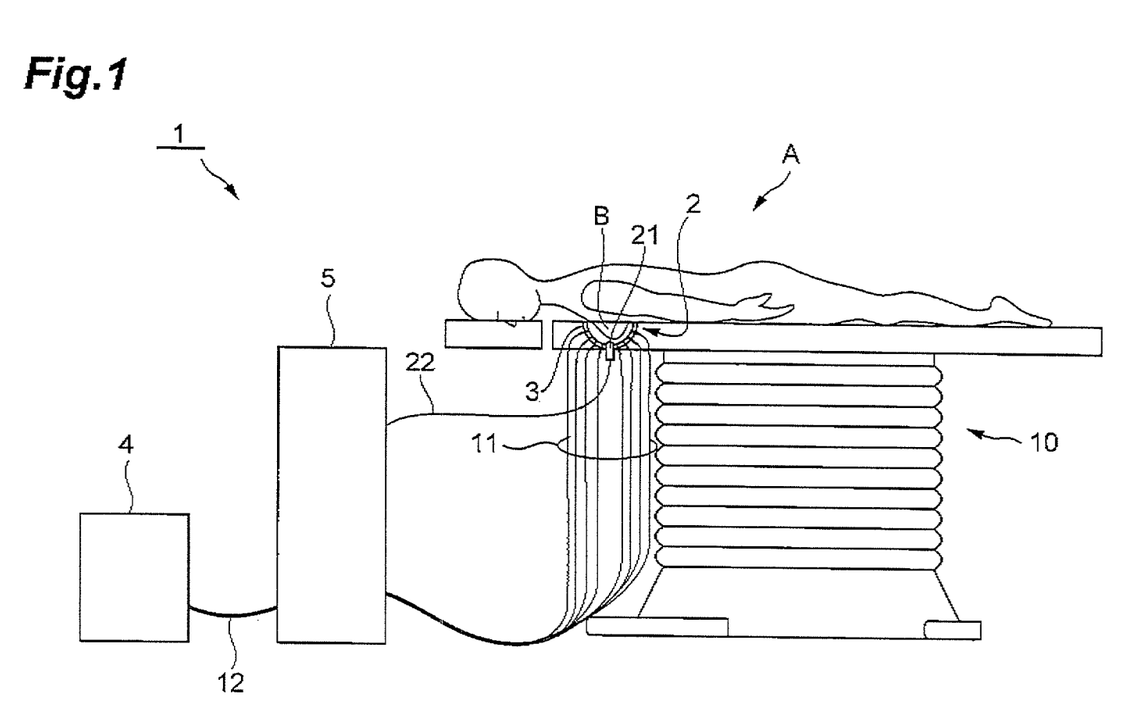
FIG. 1 is a diagram conceptually illustrating the structure of one embodiment of the breast measurement apparatus.

FIG. 1 is a diagram conceptually illustrating the structure of one embodiment of the breast measurement apparatus. The breast measurement apparatus 1 in accordance with this embodiment is an apparatus for emitting light and an ultrasonic wave to a breast of a subject, receiving transmitted scattered light (diffused reflected light) and reflected ultrasonic wave, so as to acquire an inner image of the breast, and examining whether or not there is a tumor or the like according to the inner image.

Referring to FIG. 1, a breast measurement apparatus 1 is equipped with a bed (base) 10 for a subject A to lie prone, while a hemispherical receptacle 3 for surrounding a breast 13 plumb down from the subject A is attached to the bed 10. The receptacle 3 is a support member for supporting a plurality of optical fibers 11 and an ultrasonic probe (probe) 21. That is, a plurality of optical fibers 11 for emitting and detecting examination light, each of which has one end secured to the receptacle 3 so as to face the inside thereof, and one ultrasonic probe 21 for scanning and detecting an ultrasonic wave, which is attached to the receptacle 3 so as to face the inside thereof, constitute a measurement unit (gantry) 2.

The breast measurement apparatus 1 also comprises a light source device 4 and a measurement device 5. The light source device 4 generates light to be emitted to the inside of the receptacle 3. The measurement device 5 produces an optical CT image (first inner image) of the breast B according to the examination light emitted from the light source device 4 and a signal obtained from the measurement unit 2. The measurement device 5 also produces an ultrasonic image (second inner image) of the breast B according to a reception signal concerning a reflected wave obtained from the ultrasonic probe 21.

The other end of each of the plurality of optical fibers 11 is optically connected to the measurement device 5, while the light source device 4 and the measurement device 5 are optically connected to each other through an optical fiber 12. The light source device 4 and the measurement device 5 may be connected in time alignment with each other through an electric cable. The ultrasonic probe 21 is electrically connected to the measurement device 5 through a signal cable 22.

Figure 2:
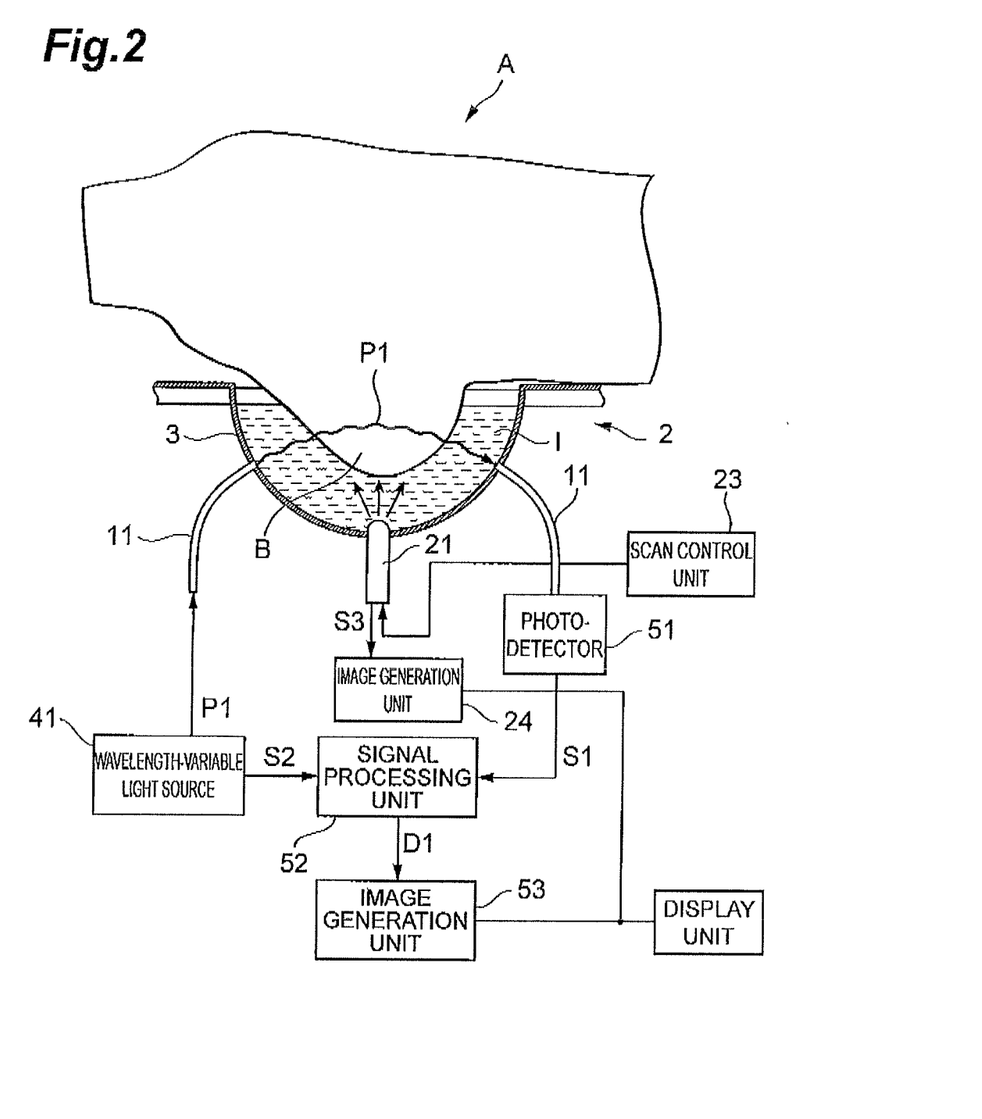
FIG. 2 is a block diagram illustrating a functional structure of the breast measurement apparatus.

FIG. 2 is a block diagram illustrating a functional structure of the breast measurement apparatus 1. For easier explanation, FIG. 2 depicts one each of the plurality of optical fibers 11 for irradiation and detection as representatives without showing the other optical fibers 11. As FIG. 2 illustrates, the breast measurement apparatus 1 comprises a wavelength-variable light source 41, a photodetector 51, a signal processing unit 52, an image generation unit 53, a scan control unit 23, and an image generation unit 24. Among them, the light source 41 is incorporated in the light source device 4, for example. The photodetector 51, signal processing unit 52, image generation unit 53, scan control unit 23, and image generation unit 24 are incorporated in the measurement device 5, for example.

The light source 41 is a device for generating light P1 serving as examination light, for example. Employed as the light P1 is pulsed light having such a short time width that internal information of a living body can be measured, for which a time width within the range of several nanosecond or shorter, for example, is typically selected. As the light source 41, various types such as light-emitting diodes, laser diodes, and diverse kinds of pulse diodes can be used, while a plurality of wavelengths are selectable.

From the relationship between the transmittance of the living body and the spectral absorption coefficient of an absorption component to be quantitatively determined and the like, a wavelength in a neap-infrared region on the order of 700 to 900 nm is preferred as the wavelength of the light P1 fed from the light source 41. The light P1 is caused to enter the optical fiber 11 for light irradiation. When necessary, the light source 41 is constructed such that light having a plurality of wavelength components can be made incident as measurement light.

The optical fiber 11 for light irradiation receives an input of the light P1 at an input end thereof and irradiates the breast B within the receptacle 3 with the light P1 emitted from an output end thereof. An end face of the optical fiber 11 is arranged at a predetermined light irradiation position on the inner wall of the receptacle 3. The optical fiber 11 for light detection feeds one end face thereof with the transmitted light of the light P1 emitted from the breast B and outputs this light to the photodetector 51. The end face of this optical fiber 11 is arranged at a predetermined light detection position on the inner wall of the receptacle 3.

The photodetector 51 is a device for detecting the light fed from the optical fiber 11 for light detection. The photodetector 51 produces a light detection signal S1 indicating the optical intensity of the detected light and the like. The generated light detection signal S1 is fed into the signal processing unit 52. As the photodetector 51, not only photomultipliers (PMT), but also various types such as photodiodes, avalanche photodiodes, and PIN photodiodes can be used. Preferably, the photodetector 51 has such a spectral sensitivity characteristic as to be able to sufficiently detect light having the wavelength of the light P1. When the transmitted scattered light from the breast B is weak, a photodetector having a high sensitivity or high gain is preferably used.

The signal processing unit 52, which is electrically connected to the photodetector 51 and light source 41, acquires a measurement waveform indicating a temporal change in optical intensity of the transmitted scattered light according to the light detection signal S1 detected from the photodetector 51 and a pulsed light emission trigger signal S2 from the light source 41. The signal processing unit 52 holds information of thus acquired measurement waveform as electronic data and provides the image generation unit 53 with this electronic data D1.

The image generation unit 53, which is the first inner image generation unit in this embodiment, produces an optical CT image (first inner image) concerning the breast B according to the transmitted scattered light. The image generation unit 53, which is electrically connected to the signal processing unit 52, inputs the electronic data D1 from the signal processing unit 52 and produces the optical CT image of the breast B by using the information of the measurement waveform included in the electronic data D1. The inner image is produced by employing an analytical operation according to time-resolved spectroscopy (TRS) utilizing a time-resolved waveform of the detection light or phase modulation spectroscopy (PMS) using modulated light, for example. Preferably, the image generation unit 53 further has a function to control each of the above-mentioned constituents such as the light source 41 and photodetector 51.

The scan control unit 23 controls the ultrasonic scan in the ultrasonic probe 21. In one example, the scan control unit 23 sets a direction of emitting the ultrasonic wave and a direction of detecting a reflected wave. The scan control unit 23 also sets a frequency of the ultrasonic wave emitted from the ultrasonic probe 21 and controls a drive voltage (i.e., ultrasonic power) to a plurality of ultrasonic transceivers in the ultrasonic probe 21. The scan control unit 23 further controls the plurality of ultrasonic transceivers.

The image generation unit 24, which is the second inner image generation unit in this embodiment, computes an ultrasonic image (second inner image) concerning the breast B according to a reflected wave of the ultrasonic wave. The image generation unit 24, which is electrically connected to the ultrasonic probe 21, inputs a reception signal 53 from the ultrasonic probe 21 and produces the ultrasonic image of the breast B according to the reception signal S3. The image generation unit 24 includes a receiving circuit, an analog-to-digital (A/D) converter, and an image data generator, for example. The receiving circuit amplifies a plurality of detection signals respectively issued from the plurality of ultrasonic transceivers, while the A/D converter converts the analog detection signal amplified by the receiving circuit into a digital detection signal (RF data). The image data generator produces an ultrasonic image according to the RF data.

The image generation units 53, 24 mentioned above are actualized by a computer having arithmetic means such as a CPU (Central Processing Unit) and storage means such as a memory, for example.

As FIG. 2 illustrates, the gap between the inner wall of the receptacle 3 and the breast B is filled with an interface agent I. The interface agent I is a liquid having an optical coefficient such as light-scattering coefficient adjusted substantially equal to that of a living tissue (breast B). The interface agent I is preferably prepared by measuring the optical coefficient of the breast B beforehand. In one example, one in which a color ink is added to an Intralipid solution so as to yield an optical coefficient matching that of the breast is favorably used as the interface agent I. In order for the ultrasonic wave from the ultrasonic probe 21 to propagate efficiently to the breast B, the interface agent I also takes account of acoustic characteristics. That is, the interface agent I is a liquid based on water ($H_2O$) which is the major component of living bodies, more preferably a liquid based on water deaerated so as to minimize generation of bubbles which cause noises. This allows the ultrasonic wave from the ultrasonic probe 21 to propagate efficiently to the breast B and the reflected wave from the breast B to be collected efficiently so as to return to the ultrasonic probe 21. On the other hand, the generation of bubbles optically distort the measurement light propagating through the interface agent in optical measurement and impart errors to the measurement light having measured the breast in the optical measurement. The deaerated water performs important actions for both ultrasonic measurement and optical measurement in that it can minimize the generation of bubbles.

Figure 3:
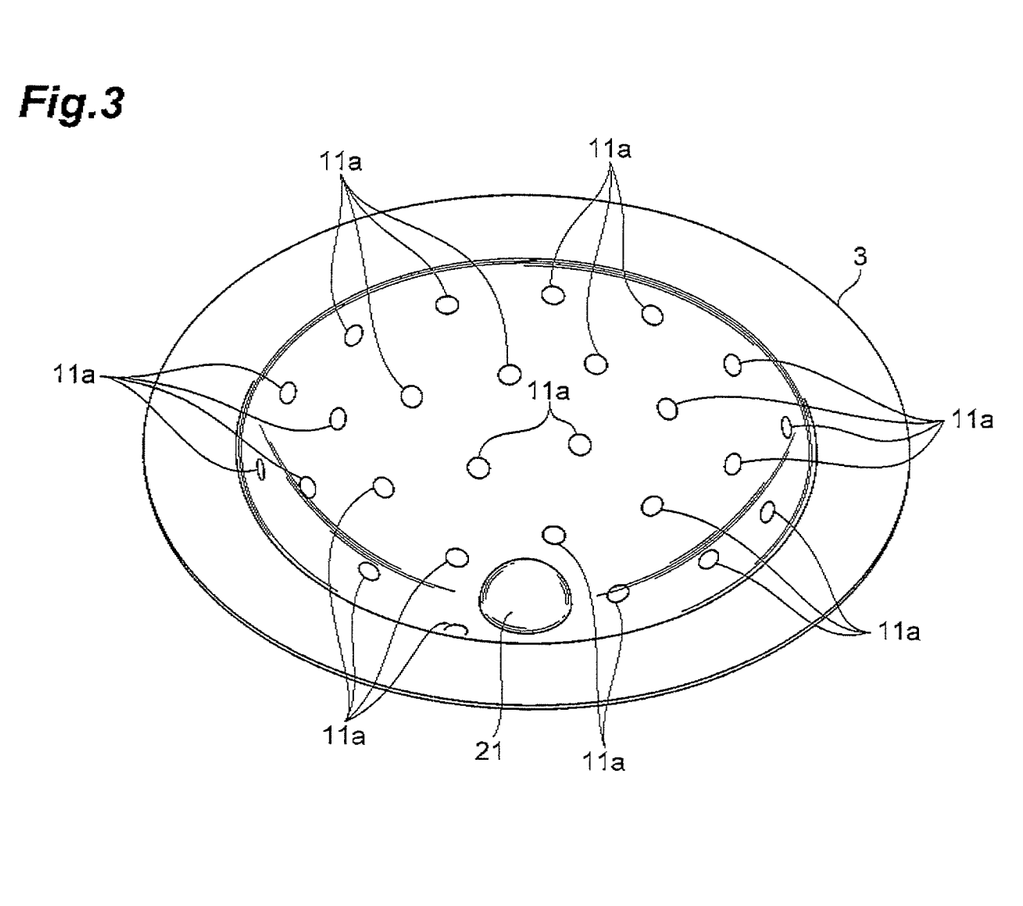
FIG. 3 is a perspective view illustrating a receptacle under magnification.

FIG. 3 is a perspective view illustrating the receptacle 3 under magnification. While the above-mentioned FIG. 2 explains the optical fibers 11 for light irradiation and light detection as represented by one each, the breast measurement apparatus 1 of this embodiment uses a great number of, e.g., 20 or more, optical fibers 11, each having one end face 11a arranged at a predetermined position on the inner wall of the receptacle 3 as illustrated in FIG. 3. A part of the optical fibers 11 are used for light irradiation, while the other part of the optical fibers 11 are used for light detection. Each optical fiber 11 may also serve for both light irradiation and light detection. For example, each optical fiber 11 may have a coaxial structure in which an optical fiber for detection is bundled around an optical fiber for irradiation; such an optical fiber 11 can favorably be attained by setting incident and light-receiving points at given points.

As FIG. 3 also illustrates, the ultrasonic probe 21 is arranged at the bottom center part of the receptacle 3. The leading end of the ultrasonic probe 21 exhibits a hemispherical form and is set such that the ultrasonic wave is emitted to the inside of the receptacle 3.

Figure 4:
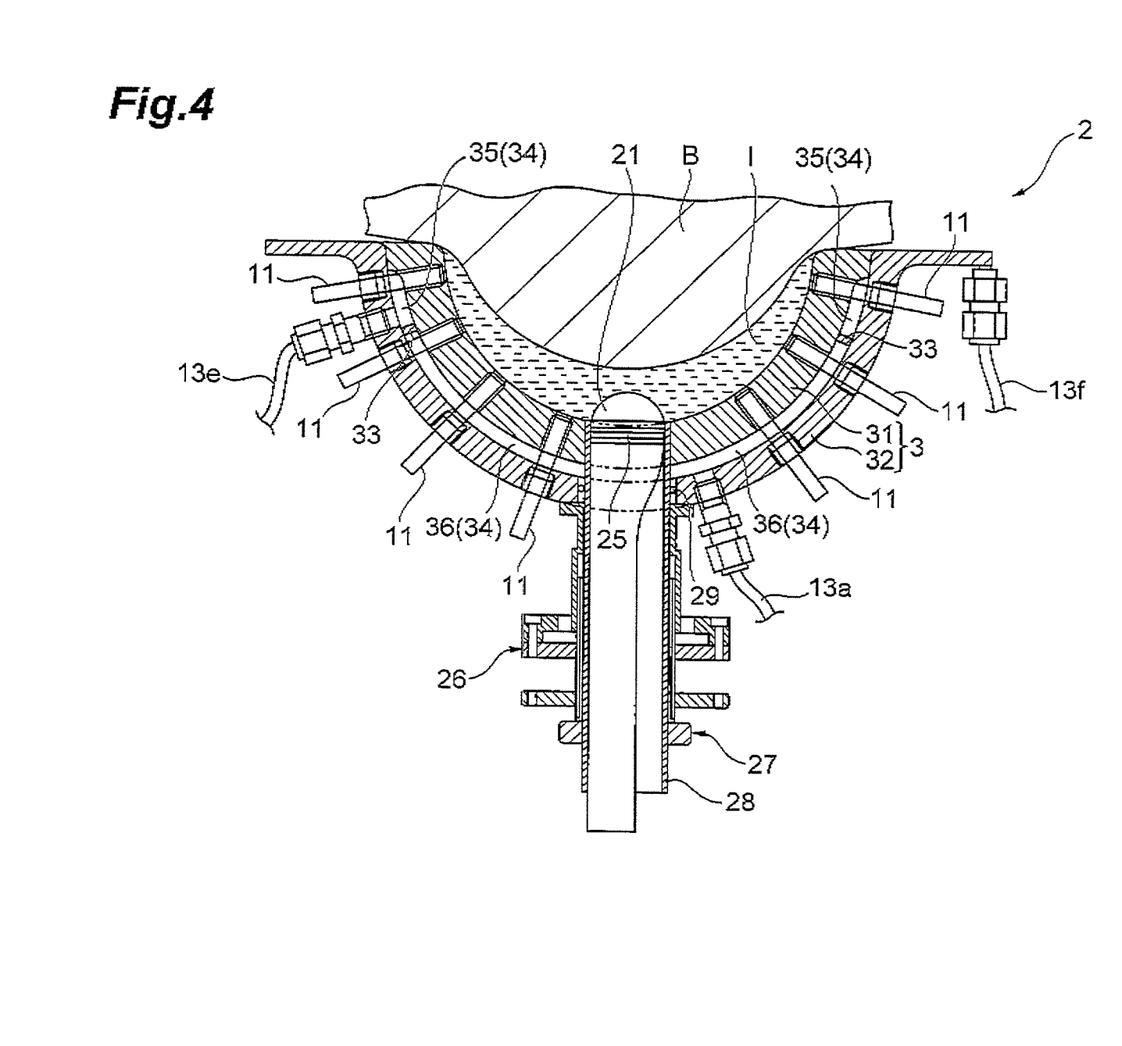
FIG. 4 is a side sectional view of a measurement unit.
Figure 5:
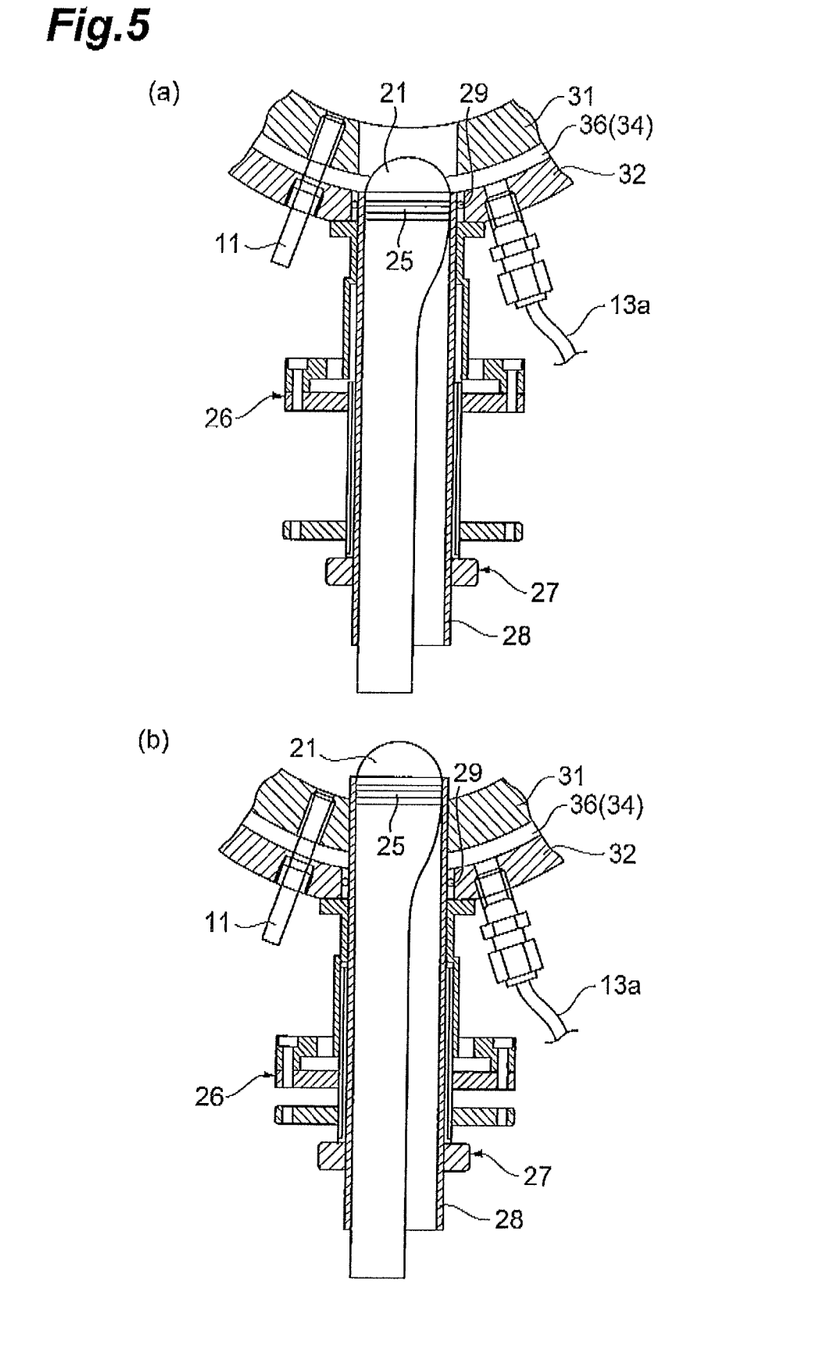
FIG. 5 is a set of diagrams illustrating how an ultrasonic probe in the measurement unit acts.

FIG. 4 is a side sectional view of the measurement unit 2. FIGS. 5(a) and 5(b) are diagrams illustrating how the ultrasonic probe 21 in the measurement unit 2 acts. Referring to FIGS. 4 and 5, the structure of the measurement unit 2 will be explained in further detail.

As FIG. 4 illustrates, the receptacle 3 of the measurement unit 2 has an inner receptacle 31 and an outer receptacle 32. The inner receptacle 31 has a hemispherical form and is arranged with its opening facing up so as to surround the breast 13 plumb down from the subject. The outer receptacle 32 has a hemispherical form greater than the inner receptacle 31 and is arranged so as to cover the outside of the inner receptacle 31. The inner and outer receptacles 31, 32 form a gap 34 therebetween.

Each of the plurality of optical fibers 11 is arranged so as to face the inside of the inner receptacle 31 and secured to the outer receptacle 32. Specifically, each optical fiber 11 is inserted through a hole formed at a predetermined position in the outer receptacle 32 and secured thereto with an undepicted holding mechanism (folder) having a seal structure for preventing the interface agent I from leaking. The inner receptacle 31 is formed with a plurality of holes for inserting the plurality of optical fibers 11, while each of the plurality of holes has an inner diameter greater than the diameter of its corresponding optical fiber 11.

The ultrasonic probe 21 is arranged so as to face the inside of the inner receptacle 31 and attached to the outer receptacle 32. The ultrasonic probe 21 is inserted through a hole formed at a predetermined position of the outer receptacle 32 (the center bottom part of the outer receptacle 32 in this embodiment). The ultrasonic probe 21 is inserted into a cylindrical tube 28 and in close contact with the inner face thereof so as to prevent the interface agent I from leaking and obstructing the scan irradiation angle of the ultrasonic wave. A seal 25 for preventing the interface agent I from leaking is provided between the tube 28 and the ultrasonic probe 21. A seal 29 for preventing the interface agent I from leaking is provided between the tube 28 and the outer receptacle 32.

As a mechanism for making a distance variable between the ultrasonic probe 21 and the breast B, a vertically operating rotary ring 26 is provided about the tube 28 of the ultrasonic probe 21. The vertically operating rotary ring 26 moves the ultrasonic probe 21 up and down as illustrated in FIGS. 5(a) and 5(b). Here, FIG. 5(a) illustrates a state where the ultrasonic probe 21 is moved down (away from the breast B), while FIG. 5(b) illustrates a state where the ultrasonic probe 21 is moved up (closer to the breast B). The ultrasonic probe 21 is located on the outside and inside of the inner face of the inner receptacle 31 in the lowest and highest states, respectively.

A rotary operation ring 27 is further provided about the tube 28 of the ultrasonic probe 21. The rotary operation ring 27 is a mechanism for rotating the ultrasonic probe 21 about an axis passing through the breast B.

A partition 33 is provided in the gap 34 between the inner and outer receptacles 31, 32. The partition 33, which is a member for dividing the gap 34, is constituted by an annular member having a surface perpendicular to both of the outer face of the inner receptacle 31 and the inner face of the outer receptacle 32. The width between the inner and outer peripheries of the partition 33 is substantially equal to the gap between the outer face of the inner receptacle 31 and the inner face of the outer receptacle 32, so as to divide the gap 34 completely.

The gap 34 is divided by the partition 33 into a distribution chamber 35 on the upper side and a drainage chamber 36 on the lower side. A pipe 13e is connected to the distribution chamber 35, while a pipe 13a is connected to the drainage chamber 36. The pipe 13e is a first pipe for injecting the interface agent I into the distribution chamber 35. The pipe 13a is a second pipe for discharging the interface agent I from the drainage chamber 36. The interface agent I flows into the distribution chamber 35 through the pipe 13e and then oozes into the inside of the inner receptacle 31 through the gap between the inner receptacle 31 and the optical fiber 11. Thereafter, the interface agent I moves on the inside of the inner receptacle 31, flows into the drainage chamber 36 through the gap between the inner receptacle 31 and the optical fiber 11, and is discharged through the pipe 13a.

A pipe 13f is also arranged on the outside of the opening of the outer receptacle 32. This pipe 13f is provided in order to discharge the interface agent I spilled out of the inner receptacle 31.

In order for the optical CT measurement by the optical fibers 11 and the ultrasonic measurement by the ultrasonic probe 21 to be performed on the inside of the inner receptacle 31, it is desirable for the inner receptacle 31 to include a material which transmits the ultrasonic wave therethrough and satisfies a boundary condition (e.g., absorption, reflection, or diffusion) of a light propagation model for the examination light. For such a reason, the inner receptacle 31 is constituted by a black resin.

In the conventional optical CT, a metal material in which a surface of an aluminum material or the like is alumite-finished for matting has been used for the inner receptacle in order to reduce invasion by ambient light and reflections within the receptacle. However, it is desirable for this embodiment to minimize noises caused by scattering and reflections of the ultrasonic wave emitted from the ultrasonic probe 21 or returning after being reflected by the breast B in the ultrasonic measurement. Therefore, a resin which reflects sonic wave less than metals do is employed as a material for the inner receptacle 31. For attaining an optical blocking effect and absorptivity with respect to near-infrared light, the inner receptacle 31 is painted black and has an appropriate thickness (e.g., approximately on the order of 5 mm to 20 mm). In one example, the inner receptacle 31 is constituted by black polyacetal having a thickness of 15 mm.

Figure 6:
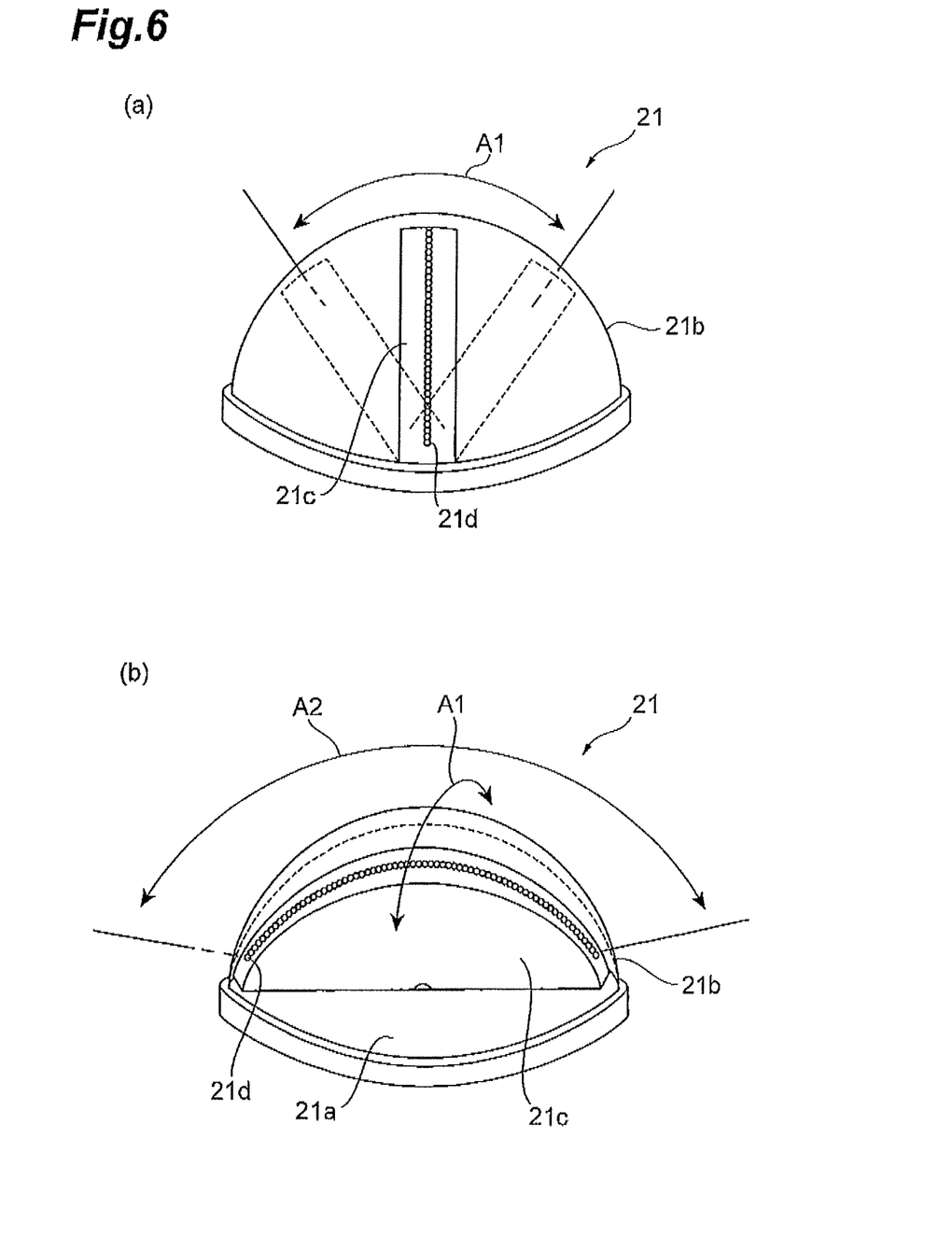
FIG. 6 is a set of diagrams illustrating an inner structure of the ultrasonic probe.

FIGS. 6(a) and 6(b) are diagrams illustrating an inner structure of the ultrasonic probe 21. The ultrasonic probe 21 in this embodiment is a so-called convex probe. As FIGS. 6(a) and 6(b) illustrate, the ultrasonic probe 21 has a hemispherical cover 21b disposed on a mount surface 21a, a half-disk-shaped support member 21c supported so as to be rotatable about an axis extending along the mount surface 21a within the cover 21b, and a plurality of transceivers 21d arranged in a row on the outer periphery of the support member 21c. FIG. 6(a) illustrates the structure of the ultrasonic probe 21 as seen in the rotary axis of the support member 21c, while FIG. 6(b) illustrates the structure of the ultrasonic probe 21 as seen in a direction orthogonal to the rotary axis of the support member 21c. In FIGS. 6(a) and 6(b), arrow A1 indicates an operation range of the support member 21c (i.e., scan range within a plane perpendicular to the rotary axis of the support member 21c).

The plurality of transceivers 21d, which are arranged in a row circumferentially of the support member 21c, send an ultrasonic wave widened like a fan and receive a reflected wave. Arrow A2 in FIG. 6(b) indicates an emission angle (i.e., scan range within a plane including the rotary axis of the support member 21c) of the ultrasonic wave sent by the plurality of transceivers 21d. When the ultrasonic probe 21 outputs the ultrasonic wave, the transceivers 21d send and receive the ultrasonic wave sequentially from the one located at the farthest part. Alternatively, a so-called electronic sector scheme in which all the transceivers 21d perform the sending and receiving at the same time may be employed.

A circulation system for the interface agent I will now be explained. As FIG. 4 illustrates, the gap between the inner wall of the receptacle 3 and the breast B is filled with the interface agent I. The interface agent I can make the optical coefficient constant between the inside and outside of the breast B, so that the boundary condition at the time of arithmetic operation by the image generation unit 53 is fixed regardless of the size of the breast B, whereby the internal information of the breast B can be computed more easily. This can also inhibit the ultrasonic wave from the ultrasonic probe 21 from being reflected by the surface of the breast B, so as to make it unnecessary for the ultrasonic probe 21 to come into contact with the breast B, and suppress attenuation of the reflected wave from the breast B. Favorably usable as an example of the interface agent I is a liquid formed by mixing an appropriate amount of a light-scattering material (e.g., Intralipid® which is an intravenous lipid emulsion) with deionized water (e.g., distilled water) in order to attain a light-scattering coefficient coinciding with that of the living body and mixing an appropriate amount of a light-absorbing material (e.g., carbon ink) therewith in order to attain a light absorption coefficient coinciding with that of the living body. The deionized water constituting the interface agent I is preferably one in which bubbles are eliminated by a deaerator or the like. This can inhibit ultrasonic noises from occurring in the interface agent I, thereby enhancing the accuracy in ultrasonic measurement.

Intralipid and carbon ink are hydrophobic. When such light-scattering and -absorbing materials included in the interface agent I are hydrophobic, they are likely to sediment in the interface agent I within the receptacle 3 as time passes. When these materials sediment, the optical coefficient of the interface agent I may become uneven, thereby lowering the accuracy in detecting transmitted scattered light. For preventing such light-scattering and -absorbing materials from sedimenting, the breast measurement apparatus 1 of this embodiment further comprises a structure for stirring the interface agent I on the outside of the receptacle 3 while circulating the interface agent I between the inside and outside of the receptacle 3.

Figure 7:
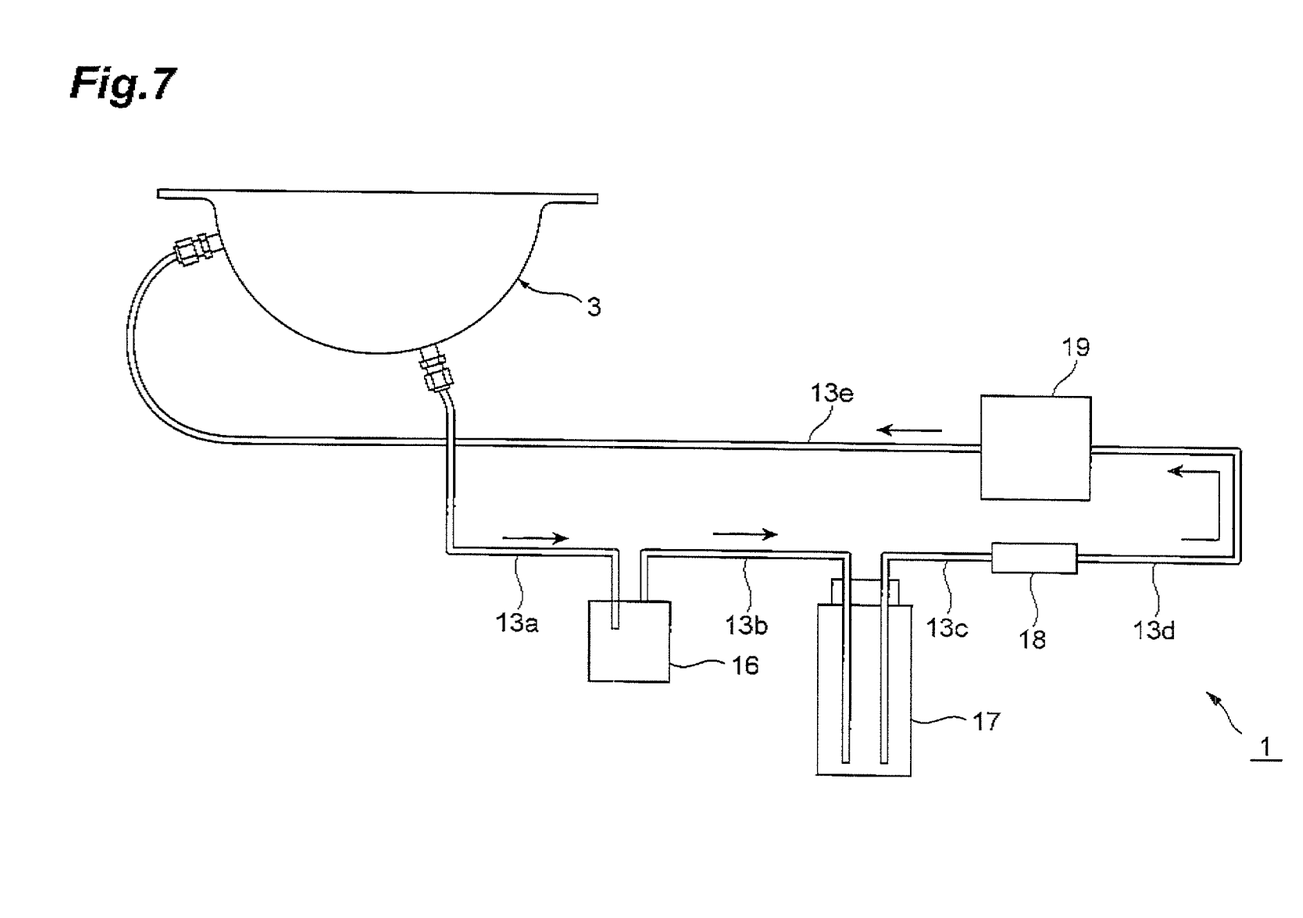
FIG. 7 is a diagram illustrating an example of structures for circulating and stirring an interface agent.

FIG. 7 is a diagram illustrating an example of structures for circulating and stirring the interface agent I. As FIG. 7 illustrates, the breast measurement apparatus 1 further comprises a circulation pump 16 for circulating the interface agent I, a tank 17 for reserving and stirring the interface agent I, a deaerator (defoamer) 18 for eliminating air and bubbles dissolved in the interface agent I, and a heater 19 for heating the interface agent I. These devices can heat and circulate the interface agent I and prevent it from precipitating and becoming uneven within the gantry. The deaerator 18 eliminates bubbles in the interface agent I and thus can inhibit ultrasonic noises from occurring in the interface agent I, thereby improving the accuracy in ultrasonic measurement. On the other hand, it is optically important to eliminate bubbles, since they optically distort the measurement light propagating through the interface agent in optical measurement and impart errors to the measurement light having measured the breast. Thus, the deaerator 18 performs important actions for both ultrasonic measurement and optical measurement.

The circulation pump 16 is connected to the receptacle 3 through the pipe 13a, so that the interface agent I is drawn into the circulation pump 16 from the receptacle 3 through the pipe 13a. The circulation pump 16 is also connected to the tank 17 through a pipe 13b, so that the interface agent I is fed to the tank 17 through the pipe 13b. An undepicted stirrer is attached to the inside of the tank 17, so as to stir the reserved interface agent I. The tank 17 is connected to the deaerator 18 through a pipe 13c, so that the stirred interface agent I is fed to the deaerator 18 through the pipe 13c. The interface agent I is depressurized in the deaerator 18, so as to eliminate bubbles and dissolved gas components. The deaerator 18 is connected to the heater 19 through a pipe 13d, so that the defoamed (deaerated) interface agent I is fed to the heater 19 through the pipe 13d. Since the subject feels uncomfortable when the interface agent I is too cold, the heater 19 heats the interface agent I to the body temperature. The heater 19 is connected to the receptacle 3 through the pipe 13e, so that the interface agent I is fed to the receptacle 3 again through the pipe 13e. Thus, the interface agent I circulates between the inside and outside of the receptacle 3 while being stirred. The order of connections among the circulation pump 16, tank 17, deaerator 18, and heater 19 may be changed when necessary, so as to be optimized.

The breast measurement apparatus 1 in accordance with this embodiment exhibits the following operations and effects. In this breast measurement apparatus 1, the ultrasonic probe 21 for scanning the breast B with the ultrasonic wave is arranged in addition to a plurality of optical fibers 11 for optical CT in the receptacle 3 surrounding the breast B. This makes it possible to acquire an optical CT image and an ultrasonic image simultaneously under the same measurement condition, so that the optical CT image and ultrasonic image can accurately be compared with each other, whereby the optical CT image can be evaluated precisely. By additionally furnishing the breast measurement apparatus 1 with an image combination unit for combining (e.g., superimposing) the optical CT image and ultrasonic image together, a measurement apparatus more useful for diagnosing breast cancer and the like can be provided.

Irradiating the breast B with the ultrasonic wave through the interface agent I as in this embodiment can inhibit the ultrasonic wave from being reflected by the surface of the breast B. This makes it unnecessary for the ultrasonic probe 21 to come into contact with the breast B, so as to ease the subject's discomfort and reduce deformations of the breast B at the time of measurement. It can also suppress attenuation of reflected waves from the breast B.

Preferably, as in this embodiment, the inner receptacle 31 of the receptacle 3 includes a material which absorbs the examination light and ultrasonic wave but blocks light from the outside. This can favorably achieve both optical CT measurement and ultrasonic measurement within the single receptacle 3.

Preferably, as in this embodiment, a mechanism (vertically operating rotary ring 26) for making a distance variable between the ultrasonic probe 21 and the breast B is provided. Preferably, as in this embodiment, a mechanism (rotary operation ring 27) for rotating the ultrasonic probe 21 about an axis passing through the breast B is provided.

If ultrasonic scanning is performed by rotating a fan-shaped ultrasonic wave about an axis when the ultrasonic probe 21 is arranged at the center bottom part of the receptacle 3 as in this embodiment, for example, an area deviating from a measurement region of ultrasonic measurement will occur on the inside of the receptacle 3. Providing the vertically operating rotary ring 26 and rotary operation ring 27 can reduce such an area.

The breast measurement apparatus in accordance with the present invention is not limited to the above-mentioned embodiment, but may be modified in various ways. For example, without being restricted to the convex probe employed as the ultrasonic probe in the above-mentioned embodiment, various types can be used as the probe in the present invention.

While the above-mentioned embodiment divides the gap between the inner and outer receptacles into upper and lower gaps, which are employed as the distribution and drainage chambers, respectively, the upper and lower gaps may be used as the drainage and distribution chambers, respectively, instead. The latter structure is suitable for eliminating bubbles emerging within the receptacle, for example. The gap between the inner and outer receptacles may be divided along directions other than the vertical direction, and one or both of the distribution and drainage chambers may be divided into a plurality of chambers.

While the above-mentioned embodiment exemplifies the inner and outer receptacles by hemispherical ones, various other forms such as columnar and conical ones, for example, are also employable.

INDUSTRIAL APPLICABILITY

The present invention can be utilized as a breast measurement apparatus which can acquire an optical CT image and an ultrasonic image under the same measurement condition.

REFERENCE SIGNS LIST

1 . . . breast measurement apparatus; 2, . . . measurement unit; 3 . . . receptacle; 4 . . . light source device; 5 . . .

measurement device; 10 ... bed; 11, 12 ... optical fiber; 13a to 13f ... pipe; 16 ... circulation pump; 17 ... tank; 18 ... deaerator; 19 ... heater; 21 ... ultrasonic probe; 31 ... inner receptacle; 32 ... outer receptacle; 33 ... partition; 34 ... gap; 35 ... distribution chamber; 36 ... drainage chamber; I ... interface agent

The invention claimed is:

1. A breast measurement apparatus for acquiring an inner image of a breast of a subject, the apparatus comprising:
   a receptacle for surrounding the breast;
   a plurality of optical fibers, arranged so as to face the inside of the receptacle, for irradiating the breast with examination light and detecting transmitted scattered light from the breast;
   a first inner image generation unit for generating a first inner image concerning the breast according to a detection signal of the transmitted scattered light;
   a probe, arranged so as to face the inside of the receptacle, for scanning the breast with an ultrasonic wave and receiving a reflected wave from the breast;
   a second inner image generation unit for generating a second inner image concerning the breast according to the reflected wave; and
   a mechanism for injecting and discharging a liquid interface agent into and from the inside of the receptacle.

2. A breast measurement apparatus according to claim 1, wherein the receptacle includes a material transmitting the ultrasonic wave therethrough and satisfying a boundary condition of a light propagation model for the examination light.

3. A breast measurement apparatus according to claim 2, wherein the receptacle includes a resin.

4. A breast measurement apparatus according to claim 1, further comprising a mechanism for making a distance variable between the probe and the breast.

5. A breast measurement apparatus according to claim 1, further comprising a mechanism for rotating the probe about an axis passing through the breast.

6. A breast measurement apparatus according to claim 1, further comprising a deaerator for deaerating the interface agent.

7. A breast measurement apparatus according to claim 1, wherein
   the second inner image generation unit is configured to extract a contour of the breast from the second inner image, and
   the first inner image generation unit is configured to construct the first image using the contour as forecast information.

8. A breast measurement apparatus according to claim 1, further comprising an image combination unit for combining the second inner image with the first inner image.

* * * * *